(12) United States Patent
Butler et al.

(10) Patent No.: US 7,195,590 B2
(45) Date of Patent: Mar. 27, 2007

(54) SURGICAL DEVICE

(75) Inventors: John Butler, County Dublin (IE); Trevor Vaugh, County Offaly (IE); Frank Bonadio, County Dublin (IE)

(73) Assignee: Atropos Limited, County Wicklow (IE)

( * ) Notice: Subject to any disclaimer, the term of this patent is extended or adjusted under 35 U.S.C. 154(b) by 328 days.

(21) Appl. No.: 10/635,909

(22) Filed: Aug. 7, 2003

(65) Prior Publication Data

US 2004/0097793 A1    May 20, 2004

Related U.S. Application Data

(63) Continuation-in-part of application No. 10/618,848, filed on Jul. 15, 2003, now abandoned, which is a continuation of application No. 09/804,418, filed on Mar. 13, 2001, now Pat. No. 6,623,426, which is a continuation of application No. PCT/IE99/00127, filed on Dec. 1, 1999.

(30) Foreign Application Priority Data

| Dec. 1, 1998 | (IE) | 980999 |
|---|---|---|
| Feb. 15, 1999 | (IE) | 990107 |
| Feb. 15, 1999 | (IE) | 990108 |
| Feb. 15, 1999 | (IE) | 990110 |
| Feb. 15, 1999 | (IE) | 990112 |
| May 24, 1999 | (IE) | 990416 |

(51) Int. Cl.
*A61B 17/00* (2006.01)

(52) U.S. Cl. .................. 600/207; 600/208; 600/206

(58) Field of Classification Search ................ 600/206, 600/207, 208, 213, 215
See application file for complete search history.

(56) References Cited

U.S. PATENT DOCUMENTS

| 1,598,284 | A | 8/1926 | Kinney |
|---|---|---|---|
| 3,244,169 | A | 4/1966 | Baxter |
| 3,347,226 | A | 10/1967 | Harrower |
| 3,347,227 | A | 10/1967 | Harrower |
| 3,397,692 | A | 8/1968 | Creager et al. |
| 3,522,800 | A | 8/1970 | Lesser |
| 3,797,478 | A | 3/1974 | Walsh et al. |
| 3,915,171 | A | 10/1975 | Shermeta |
| 4,228,792 | A | 10/1980 | Rhys-Davies |
| 5,045,070 | A | 9/1991 | Grodecki et al. |

(Continued)

FOREIGN PATENT DOCUMENTS

DE            37 39 532          12/1988

(Continued)

OTHER PUBLICATIONS

Original Specification of U.S. Appl. No. 09/801,826, filed Mar. 9, 2001.

*Primary Examiner*—Cary E. O'Connor
(74) *Attorney, Agent, or Firm*—Finnegan, Henderson, Farabow, Garrett & Dunner, LLP

(57) ABSTRACT

A wound retractor comprises a retracting member for insertion into a wound opening and a proximal member for location member for location externally of a wound opening. The proximal member is movable relative to the retracing member to shorten the axial extent of the retracting member to laterally retract a wound opening. The retracted wound opening is retracted by a seal which is integral with the retractor.

25 Claims, 8 Drawing Sheets

U.S. PATENT DOCUMENTS

| | | | |
|---|---|---|---|
| 5,158,553 | A | 10/1992 | Berry et al. |
| 5,161,773 | A | 11/1992 | Tower |
| 5,213,114 | A | 5/1993 | Bailey, Jr. |
| 5,342,385 | A | 8/1994 | Norelli et al. |
| 5,350,364 | A | 9/1994 | Stephens et al. |
| 5,364,345 | A | 11/1994 | Lowery et al. |
| 5,366,478 | A | 11/1994 | Brinkerhoff et al. |
| 5,391,156 | A | 2/1995 | Hildwein et al. |
| 5,480,410 | A | 1/1996 | Cuschieri et al. |
| 5,514,133 | A | 5/1996 | Golub et al. |
| 5,522,791 | A | 6/1996 | Leyva |
| 5,524,644 | A | 6/1996 | Crook |
| 5,526,536 | A | 6/1996 | Cartmill |
| 5,545,179 | A | 8/1996 | Williamson, IV |
| 5,634,911 | A | 6/1997 | Hermann et al. |
| 5,634,937 | A | 6/1997 | Mollenauer et al. |
| 5,636,645 | A | 6/1997 | Ou |
| 5,640,977 | A | 6/1997 | Leahy et al. |
| 5,649,550 | A | 7/1997 | Crook |
| 5,653,705 | A | 8/1997 | de la Torre et al. |
| 5,672,168 | A | 9/1997 | de la Torre et al. |
| 5,741,234 | A | 4/1998 | Aboul-Hosn |
| 5,741,298 | A | 4/1998 | MacLeod |
| 5,803,921 | A | 9/1998 | Bonadio |
| 5,810,721 | A | 9/1998 | Mueller et al. |
| 5,813,409 | A | 9/1998 | Leahy et al. |
| 5,832,925 | A | 11/1998 | Rothrum |
| 5,853,395 | A | 12/1998 | Crook et al. |
| 5,899,208 | A | 5/1999 | Bonadio |
| 5,906,577 | A | 5/1999 | Beane et al. |
| 5,947,922 | A | 9/1999 | MacLeod |
| 5,957,913 | A | 9/1999 | de la Torre et al. |
| 5,964,781 | A | 10/1999 | Mollenauer et al. |
| 5,997,515 | A | 12/1999 | de la Torre et al. |
| 6,033,426 | A | 3/2000 | Kaji |
| 6,033,428 | A | 3/2000 | Sardella |
| 6,042,573 | A | 3/2000 | Lucey |
| 6,048,309 | A | 4/2000 | Flom et al. |
| 6,077,288 | A | 6/2000 | Shimomura et al. |
| 6,110,154 | A | 8/2000 | Shimomura et al. |
| 6,142,935 | A | 11/2000 | Flom et al. |
| 6,142,936 | A | 11/2000 | Beane et al. |
| 6,254,533 | B1 | 7/2001 | Fadem et al. |
| 6,254,534 | B1 | 7/2001 | Butler et al. |
| 6,578,577 | B2 | 6/2003 | Bonadio et al. |
| 6,582,364 | B2 | 6/2003 | Butler et al. |
| 6,623,426 | B2 * | 9/2003 | Bonadio et al. ............ 600/207 |
| 2003/0078478 | A1 * | 4/2003 | Bonadio et al. ............ 600/208 |

FOREIGN PATENT DOCUMENTS

| | | |
|---|---|---|
| DE | 37 37 121 | 5/1989 |
| DE | 296 00 939 | 6/1998 |
| EP | 0950376 | 10/1999 |
| FR | 1456623 | 9/1966 |
| GB | 1151993 | 5/1969 |
| GB | 2071502 | 9/1981 |
| GB | 2255019 | 10/1992 |
| JP | 10-108868 | 4/1998 |
| WO | WO 92/11880 | 7/1992 |
| WO | WO 95/07056 | 3/1995 |
| WO | WO 95/22289 | 8/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |

* cited by examiner

SURGICAL DEVICE

This application is a Continuation-In-Part of U.S. application Ser. No. 10/618,848, filed on Jul. 15, 2003, now abandoned which is a Continuation of application Ser. No. 09/804,418, filed on Mar. 13, 2001, now U.S. Pat. No. 6,623,426 which is a Continuation of International Application No. PCT/IE99/00127, filed on Dec. 1, 1999, all of which are incorporated herein by reference. This application claims the foreign priority of Ireland Application No. 980999, filed on Dec. 1, 1998, Ireland Application No. 990107, filed on Feb. 15, 1999, Ireland Application No. 990108, filed on Feb. 15, 1999, Ireland Application No. 990110, filed Feb. 15, 1999, Ireland Application No. 990112, filed Feb. 15, 1999, and Ireland Application No. 990416, filed May 24,1999, and also claims the benefit of U.S. Provisional Application No. 60/401,759, filed on Aug. 8, 2002, all of which are incorporated herein by reference.

INTRODUCTION

This invention relates to a surgical device. In particular it relates to a surgical device for both retracting a wound opening and sealing the retracted wound opening.

STATEMENTS OF INVENTION

According to the invention there is provided a surgical device comprising:
  a wound retractor comprising:
    a retracting member for insertion into a wound opening; and
    a proximal member for location externally of a wound opening;
    the proximal member being movable relative to the retracting member to shorten the axial extent of the retracting member to laterally retract a wound opening; and
  means to seal a retracted wound opening;
  the sealing means being integral with the wound retractor.

The surgical device of the invention provides a wound retractor for retracting the sides of a wound opening, and means to seal the retracted wound opening integral with the wound retractor.

In one embodiment of the invention the proximal member comprises an annular ring means. Preferably the annular ring means comprises an inner ring and an outer ring between which the retracting member may be led. Ideally the inner ring defines a projection for location in a complementary recess of the outer ring with the retracting member located therebetween. The inner ring may be a relatively loose fit in the recess of the outer ring. The inner ring may alternatively be a relatively tight fit in the recess of the outer ring to grip the retracting member therebetween. At least portion of one of the rings is preferably movable from a rest position in which the retracting member is substantially clamped between the rings to a release position in which at least portion of the retracting member is movable relative to the rings.

In another embodiment the sealing means comprises a chamber for receiving pressurised fluid to seal a retracted wound opening. Preferably the sealing means comprises a sleeve having an inner sleeve section and an outer sleeve section with the chamber defined between the inner and outer sleeve sections. Ideally the sleeve is evertable upon advancement of an object through the sleeve.

In another aspect the invention provides a surgical device comprising:
  a retracting member movable from an insertion configuration to a retracting configuration to retract laterally a wound opening; and
  a sleeve integral with the retracting member;
  the sleeve having an inner sleeve section and an outer sleeve section with a chamber for receiving pressurised fluid between the inner and outer sleeve sections to seal a retracted wound opening;
  the sleeve being evertable upon advancement of an object through the sleeve to facilitate sealed access through a retracted wound opening.

In one case the retracting member is provided by at least portion of the outer sleeve section.

The sleeve may be turned axially back on itself to define the sleeve sections. Ideally the outer sleeve section is substantially cylindrical, and the inner sleeve section is twisted and of the same untwisted diameter as that of the outer sleeve section.

In another embodiment of the invention the device comprises a distal member coupled to a distal end of the retracting member for insertion into a wound opening. Preferably the distal member is of a resilient material. Ideally the distal member comprises an O-ring.

In a further aspect the invention provides a surgical device comprising:
  a retracting member movable from an insertion configuration to a retracting configuration to retract laterally a wound opening; and
  means to seal a retracted wound opening;
  the retracting member being integral with the sealing means.

According to another aspect of the invention there is provided a wound retractor comprising:
  a retracting member for insertion into a wound opening;
  a proximal member for location externally of a wound opening;
  the proximal member being movable relative to the retracting member to shorten the axial extent of the retracting member to laterally retract a wound opening; and
  a chamber for receiving pressurised fluid to maintain a wound opening retracted.

In one embodiment the chamber is integral with the retracting member.

The chamber preferably overlaps the proximal member to maintain a wound opening retracted. Ideally the chamber overlaps the proximal member at a proximal side of the proximal member.

In a further aspect the invention provides a method of performing a surgical procedure, the method comprising the steps of:
  inserting a surgical device into a wound opening;
  moving at least part of the surgical device laterally to retract the wound opening; and
  inflating at least part of the surgical device to maintain the wound opening retracted.

In one case the step of inflating at least part of the surgical device effects a seal of the retracted wound opening.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Figure 3:
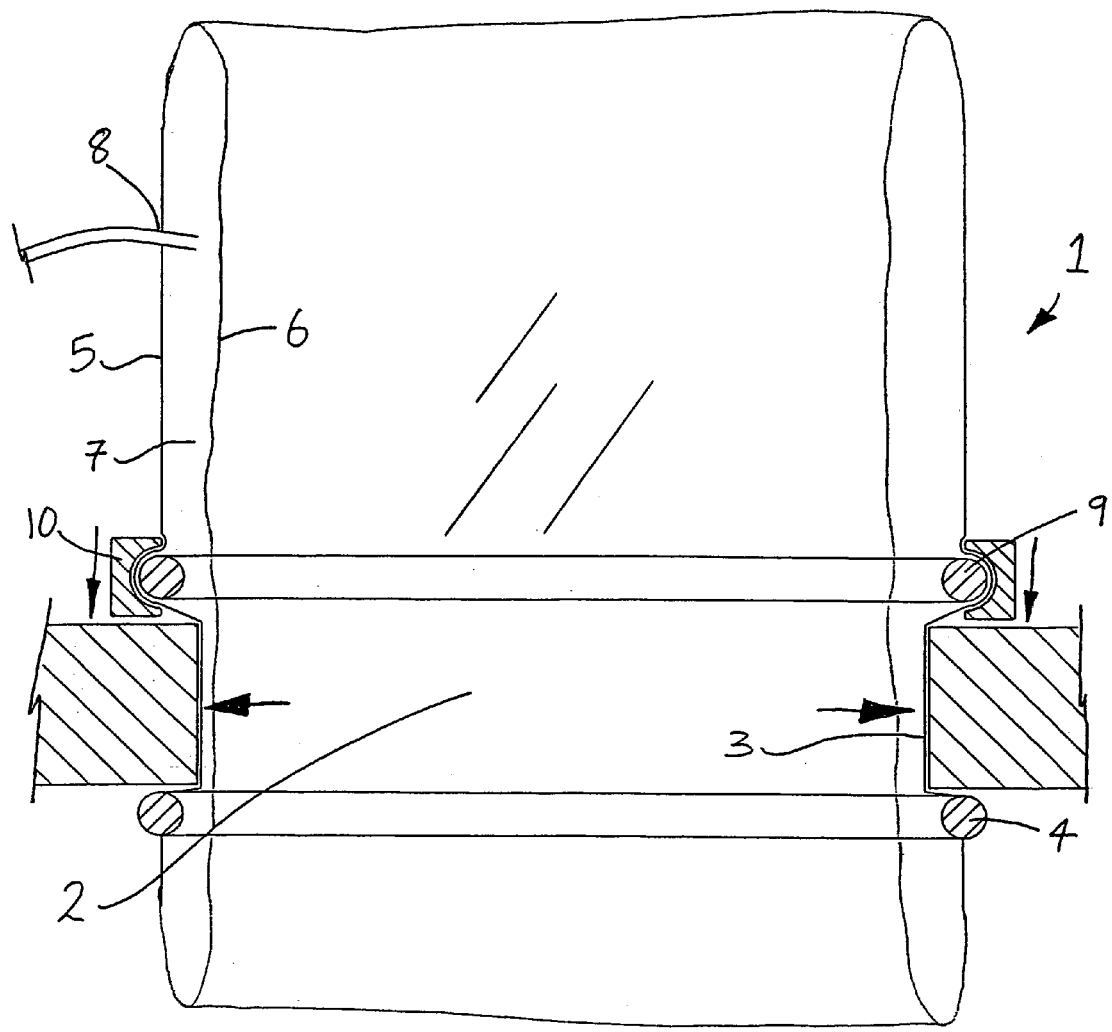
Figure 4:
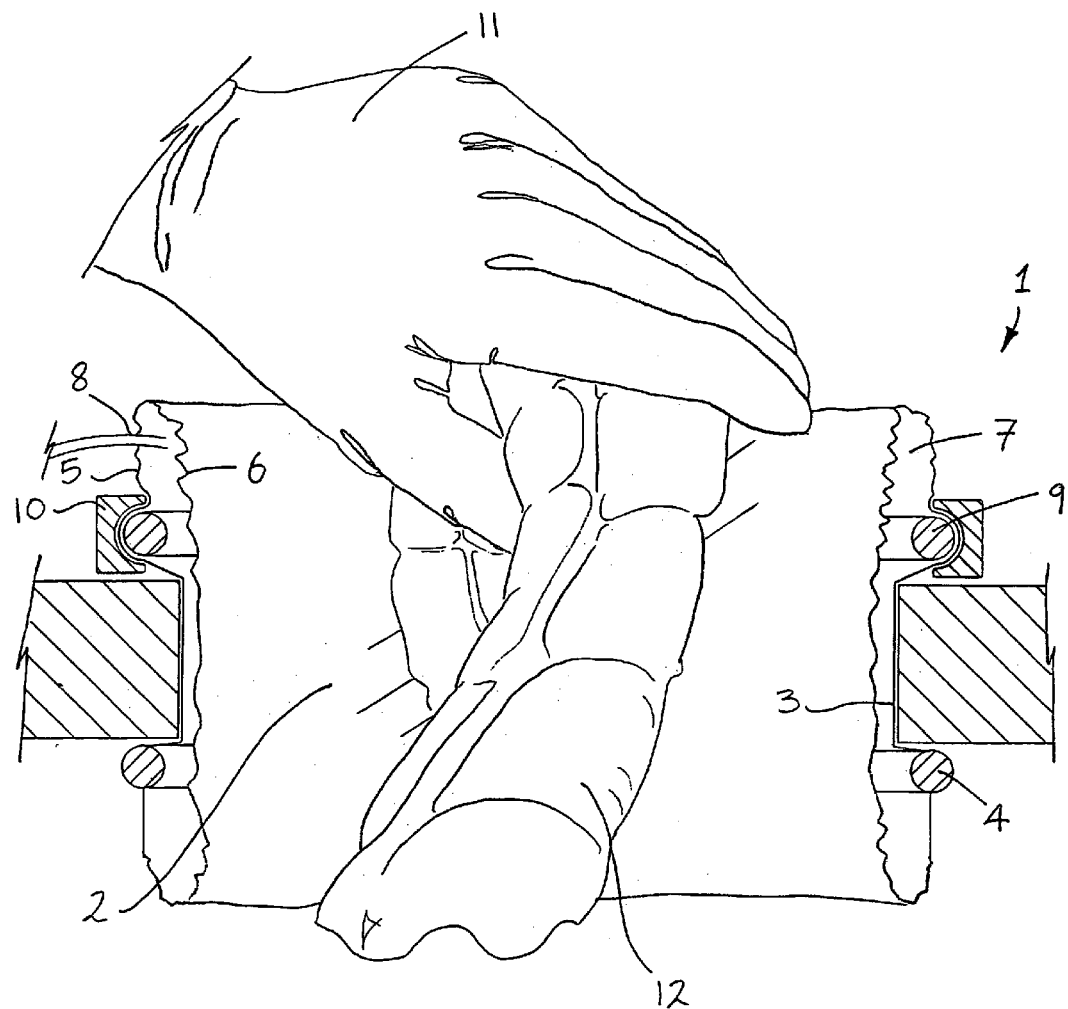

Referring to the drawings there is illustrated a surgical device 1 according to the invention. The device 1 is suitable for insertion into a wound opening 2 (FIG. 2) to retract laterally the sides of the wound opening 2 (FIGS. 3 & 4). The device 1 may then be used to seal the retracted wound opening 2 in a gas-tight manner (FIGS. 5 to 7), for example during hand assisted laparoscopic surgery or during pure laparoscopic surgery.

The device 1 comprises a sleeve 3, a distal O-ring 4 for insertion into a wound opening 2, and a proximal annular ring means for location externally of a wound opening 2.

The sleeve 3 is turned axially back on itself to define an outer sleeve section 5 and an inner sleeve section 6 with a chamber 7 between the inner and outer sleeve sections 5, 6. A pressurised fluid may be passed into the chamber 7 through an inlet port 8 to inflate the sleeve 3.

Figure 8:
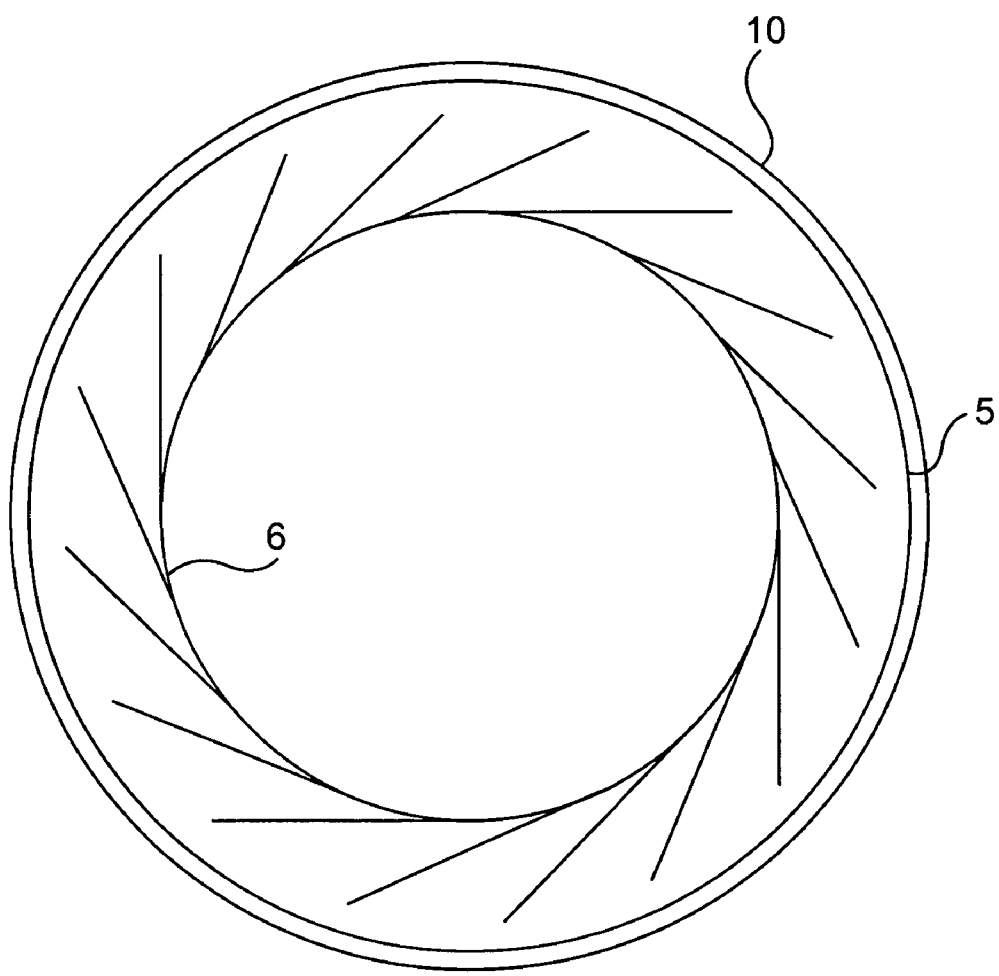
FIG. 8 is a top view of the device of FIG. 1.

The outer sleeve section 5 is substantially cylindrical, and the inner sleeve section 6 is twisted (FIG. 8) and of the same untwisted diameter as that of the outer sleeve section 5. The sleeve 3 may evert upon advancement of an object, such as a surgeon's hand, through the sleeve 3 when inflated. Upon eversion part of the inner sleeve section 6 rolls outwardly to become part of the outer sleeve section 5, and part of the outer sleeve section 5 rolls inwardly to become part of the inner sleeve section 6.

The distal O-ring 4 is of a resilient material to facilitate manipulation/scrunching-up of the O-ring 4 to enable the O-ring 4 to be inserted into a potentially narrow wound opening 2. Once inserted into the wound opening 2, the O-ring 4 acts as an anchor to maintain the device 1 in position in the wound opening 2.

The distal O-ring 4 is coupled to the sleeve 3 by any suitable means, such as by adhesively bonding the O-ring 4 to the sleeve 3.

The proximal annular ring means comprises, in this case, a proximal inner ring 9 and a proximal outer ring 10. The inner ring 9 is an O-ring and has a substantially circular cross-section, and the outer ring 10 has a substantially "C"-shaped cross-section. In this manner, the projecting inner ring 9 may be located at least partially within the complimentary recess of the outer ring 10, with the sleeve 3 extending between the inner and outer rings 9, 10.

The inner ring 9 is a relatively tight fit in the recess of the outer ring 10. This results in the sleeve 3 being gripped between the rings 9, 10. The rings 9, 10 may be moved relative to one another from a rest position in which the sleeve 3 is clamped between the rings 9, 10 to a release position in which a portion of the sleeve 3 may be moved relative to the rings 9, 10.

The proximal rings 9, 10 are moved relative to the sleeve 3 to shorten the axial extent of the portion of the sleeve 3 between the distal O-ring 4 and the proximal rings 9, 10. In this manner the sleeve 3 may be moved laterally to retract the sides of the wound opening 2, as illustrated in FIG. 3.

Figure 1:
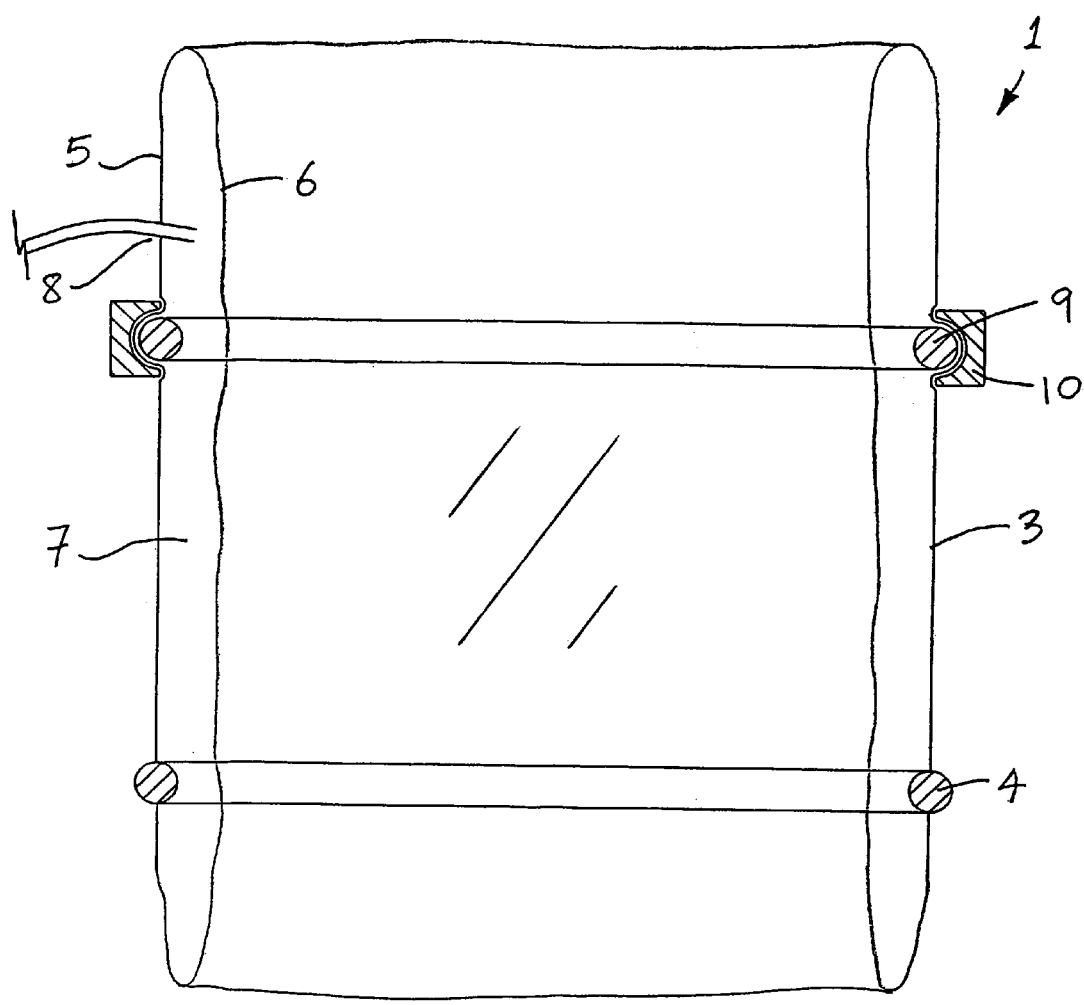
FIG. 1 is a cross-sectional, front view of a surgical device according to the invention.
Figure 2:
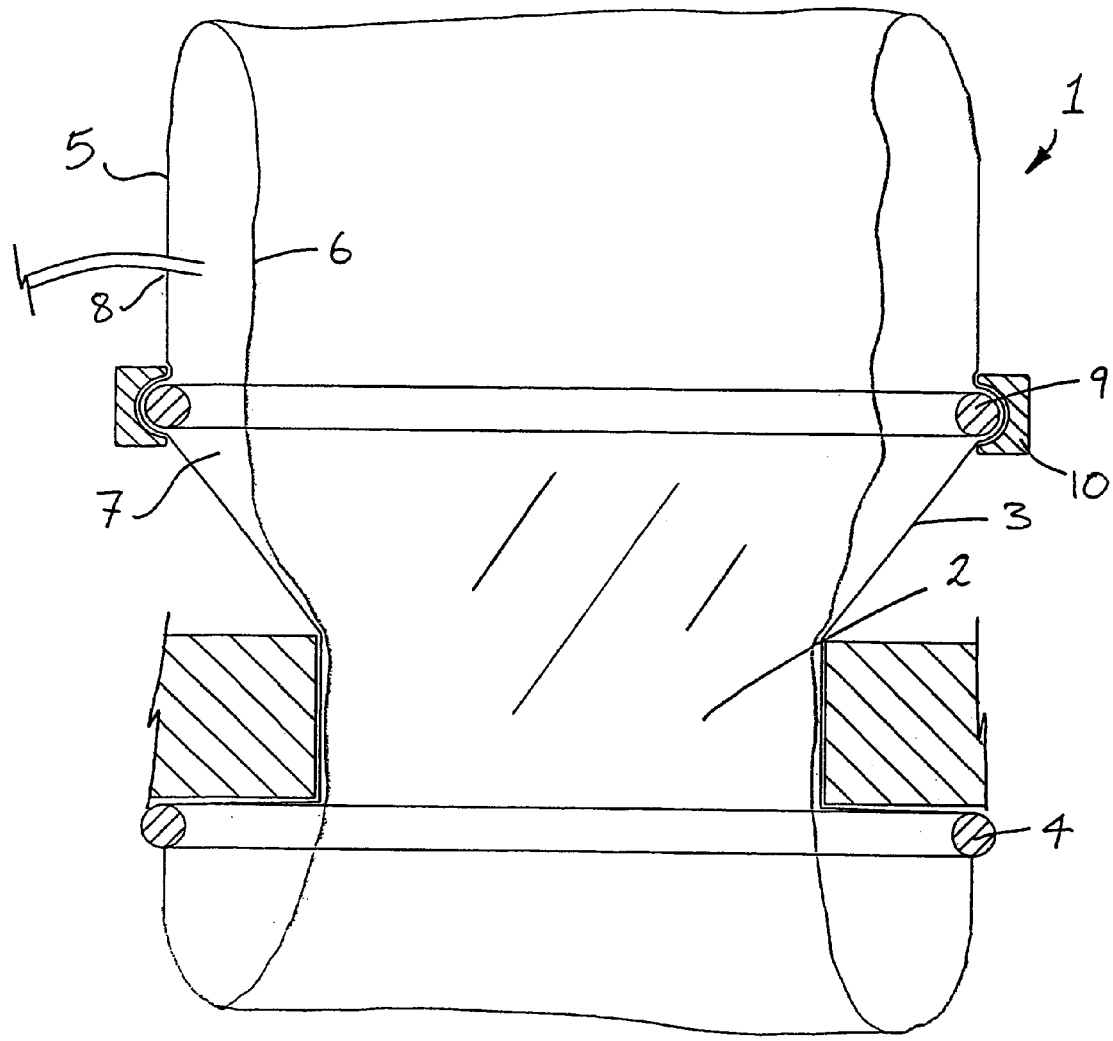
FIGS. 2 to 4 are cross-sectional, front views of the device of FIG. 1 in use retracting a wound opening.

In use, with the sleeve 3 deflated the distal O-ring 4 is manipulated/scrunched-up and inserted through the wound opening 2 (FIG. 2). The distal O-ring 4 is then released and the resilient O-ring 4 returns to the annular shape to anchor the device 1 in position in the wound opening 2. The proximal rings 9, 10 remain externally of the wound opening 2.

To retract laterally the sides of the wound opening 2, the sleeve 3 is gripped and pulled upwardly while the proximal rings 9, 10 are pushed downwardly (FIG. 3). This action shortens the axial extent of the portion of the sleeve 3 between the distal O-ring 4 and the proximal rings 9, 10, and thus causes the outer sleeve section 5 to be pressed laterally against the sides of the wound opening 2 (FIG. 3). In this way the wound opening 2 is retracted laterally.

The surgical device 1 of the invention thus enables a surgeon 11 to gain access to an internal body cavity, and/or to internal body organs 12 through the retracted wound opening 2, as illustrated in FIG. 4. In certain cases it may be desired to remove an organ from a body in part or in whole. In other cases it may be desired to extracorporealise an organ in part or in whole and then replace the organ.

Figure 5:
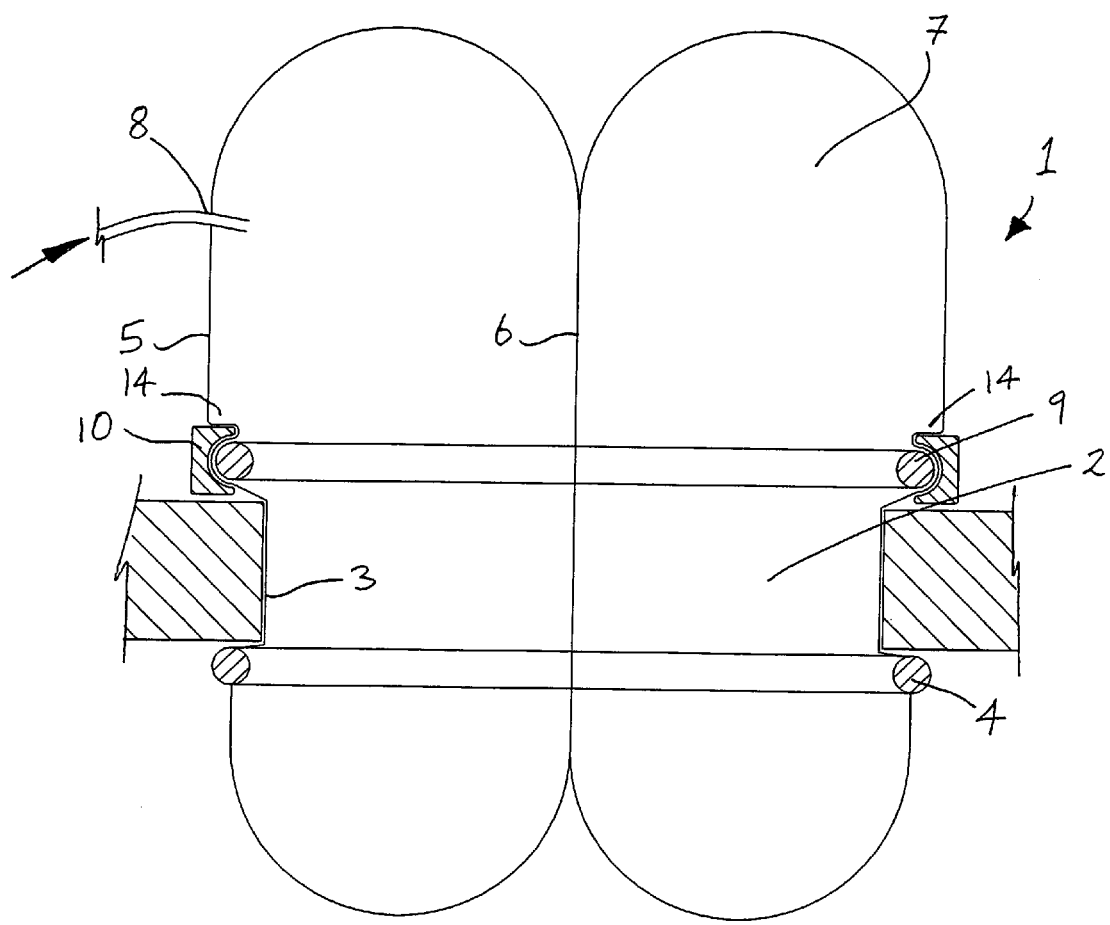
FIGS. 5 to 7 are cross-sectional, front views of the device of FIG. 1 in use sealing the retracted wound opening.

To seal the retracted wound opening 2, for example to prevent insufflation gas from escaping from an internal body cavity, a pressurised fluid, such as air, is passed through the inlet port 8 into the chamber 7 (FIG. 5). In this way, the sleeve 3 is inflated until the passageway defined through the inner sleeve section 6 is closed down, and the retracted wound opening 2 is gas-tightly sealed.

It is noted that the retraction force exerted by the sleeve 3 on the sides of the wound opening 2 during retraction of the wound opening 2, as described previously with reference to FIG. 3, also results in a particularly effective gas-tight seal between the sleeve 3 and the sides of the wound opening 2. In this manner, the possibility of the escape of insufflation gas from the body cavity between the outer sleeve section 5 and the sides of the wound opening 2 is minimised. In particular, the surgical device 1 of the invention does not rely solely on the fluid pressure within the chamber 7 to effect an effective gas-tight seal of the outer sleeve section 5 to the sides of the wound opening 2.

Figure 6:
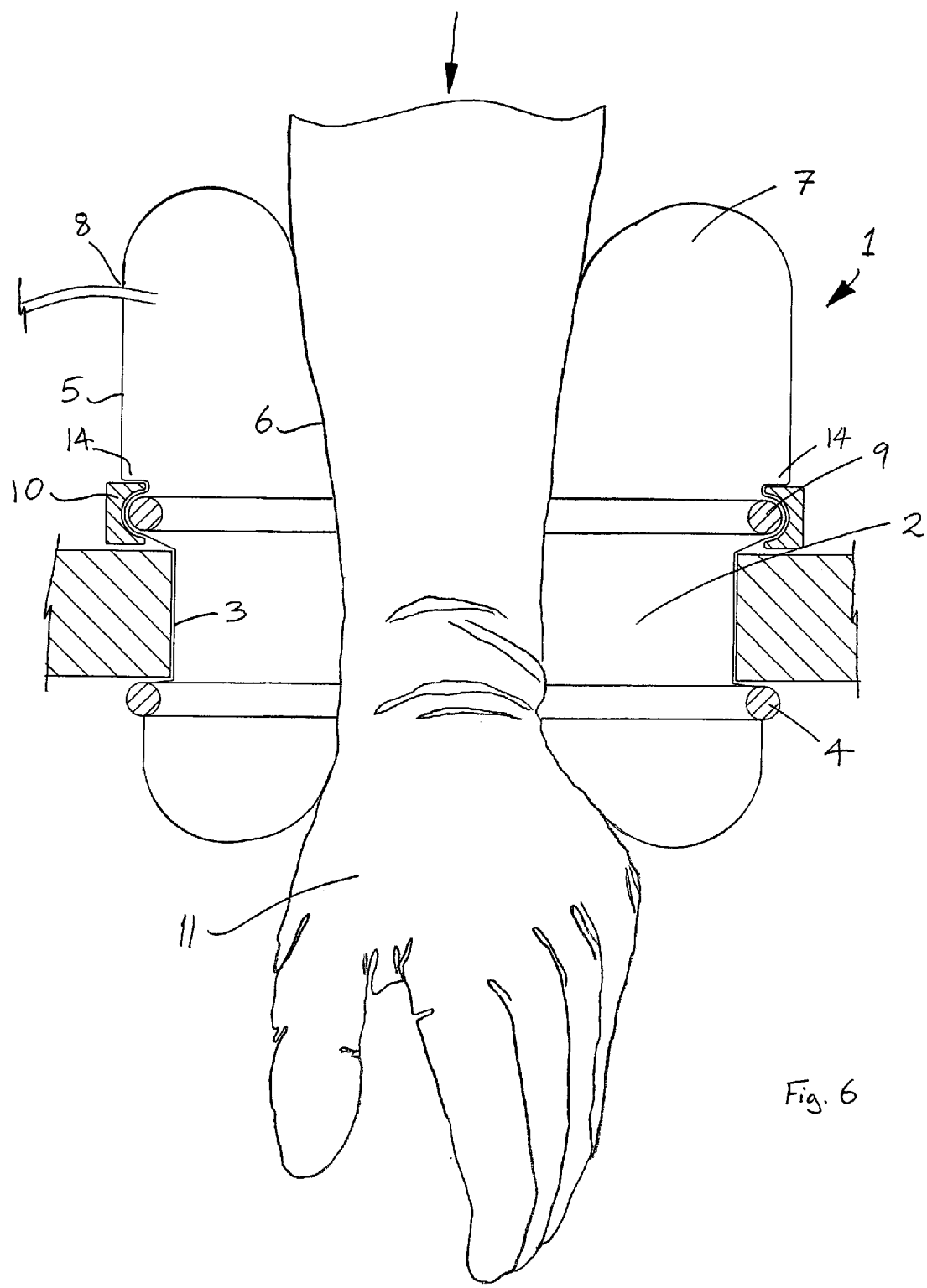

To gain access to an internal body cavity, and/or to internal body organs through the surgical device 1, a surgeon 11 may insert his hand through the inflated sleeve 3 (FIG. 6).

As the surgeon's hand passes though the sleeve 3, the sleeve 3 everts with part of the outer sleeve section 5 rolling inwardly to become part of the inner sleeve section 6, and part of the inner sleeve section 6 rolling outwardly to become part of the outer sleeve section 5. This everting action provides for an easier passage of the surgeon's hand through the inflated sleeve 3.

The inflated sleeve 3 adheres to the surgeon's hand/forearm along the twisted inner sleeve section 6 in a substantially gas-tight manner to minimise the possibility of the escape of insufflation gas from the body cavity between the inner sleeve section 6 and the surgeon's hand/forearm. The surgical device 1 thus enables access to a body cavity and/or body organs while maintaining pneumoperitoneum.

When the sleeve 3 has been inflated, the fluid pressure in the chamber 7 causes a shoulder 14 to form in the sleeve 3 above the proximal outer ring 10, as illustrated in FIG. 5. This inflated shoulder 14 acts to resist any movement of the proximal rings 9, 10 upwardly relative to the sleeve 3. Thus the inflated shoulder 14 acts as an integral locking means to maintain the axial extent of the portion of the sleeve 3 between the distal O-ring 4 and the proximal rings 9, 10 shortened, and thereby to maintain the wound opening 2 retracted. In particular no additional step of locking the device 1 in the retracted position is required to maintain the wound opening 2 retracted.

Because the proximal rings 9, 10 are moveable relative to the sleeve 3 and relative to the distal O-ring 4, this enables the surgical device 1 of the invention to be used with a wide range of abdominal wall thicknesses.

Figure 7:
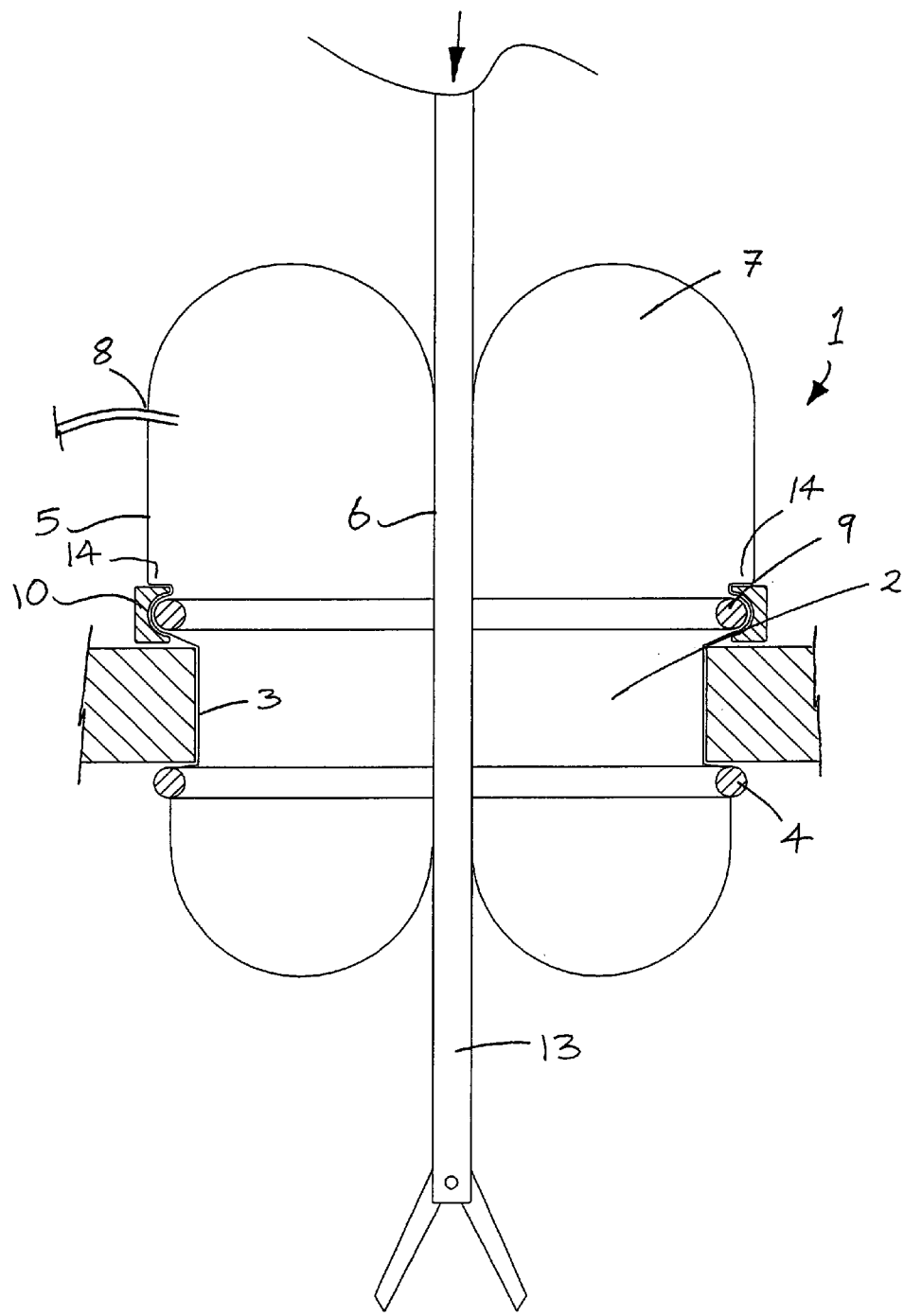

It will be appreciated that the surgical device 1 of the invention may also be used to facilitate sealed access of a variety of objects into a body cavity through the device 1. For example, a surgical instrument 13 may be inserted in a gas-tight manner through the sleeve 3, as illustrated in FIG. 7, while maintaining pneumoperitoneum.

In an alternative arrangement the inner ring 9 may be a relatively loose fit in the recess of the outer ring 10.

The invention is not limited to the embodiments hereinbefore described, with reference to the accompanying drawings, which may be varied in construction and detail.

The invention claimed is:

1. A surgical device comprising:
a wound retractor comprising:
a retracting member for insertion into a wound opening; and
a proximal member for location externally of a wound opening;
the proximal member being movable relative to the retracting member to shorten the axial extent of the retracting member to laterally retract a wound opening; and
a seal integral with the wound retractor, the seal including a chamber for receiving pressurized fluid to seal a retracted wound opening, and a sleeve having an inner sleeve section and an outer sleeve section with the chamber defined between the inner and outer sleeve sections, the sleeve being evertable upon advancement of an object through the sleeve.

2. A device as claimed in claim 1 wherein the proximal member comprises an annular ring assembly.

3. A device as claimed in claim 2 wherein the annular ring assembly comprises an inner ring and an outer ring between which the retracting member may be led.

4. A device as claimed in claim 3 wherein the inner ring defines a projection for location in a complementary recess of the outer ring with the retracting member located therebetween.

5. A device as claimed in claim 4 wherein the inner ring is a relatively loose fit in the recess of the outer ring.

6. A device as claimed in claim 4 wherein the inner ring is a relatively tight fit in the recess of the outer ring to grip the retracting member therebetween.

7. A device as claimed in claim 4 wherein at least a portion of one of the rings is movable from a rest position in which the retracting member is substantially clamped between the rings to a release position in which at least a portion of the retracting member is movable relative to the rings.

8. A device as claimed in claim 1 wherein the retracting member is provided by at least a portion of the outer sleeve section.

9. A device as claimed in claim 1 wherein the sleeve is turned axially back on itself to define the sleeve sections.

10. A device as claimed in claim 1 wherein the outer sleeve section is substantially cylindrical, and the inner sleeve section is twisted and of the same untwisted diameter as that of the outer sleeve section.

11. A surgical device comprising:
a retracting member movable from an insertion configuration to a retracting configuration to retract laterally a wound opening; and
a sleeve integral with the retracting member;
the sleeve having an inner sleeve section and an outer sleeve section with a chamber for receiving pressurized fluid between the inner and outer sleeve sections to seal a retracted wound opening, wherein the outer sleeve section is substantially cylindrical, and the inner sleeve section is twisted and of the same untwisted diameter as that of the outer sleeve section;
the sleeve being evertable upon advancement of an object through the sleeve to facilitate sealed access through a retracted wound opening.

12. A device as claimed in claim 11 wherein the retracting member is provided by at least a portion of the outer sleeve section.

13. A device as claimed in claim 11 wherein the sleeve is turned axially back on itself to define the sleeve sections.

14. A device as claimed in claim 11 wherein the device comprises a distal member coupled to a distal end of the retracting member for insertion into a wound opening.

15. A device as claimed in claim 14 wherein the distal member is of a resilient material.

16. A device as claimed in claim 14 wherein the distal member comprises an O-ring.

17. A surgical device comprising:
a wound retractor comprising:
a retracting member for insertion into a wound opening; and
a proximal member for location externally of a wound opening;
the proximal member being movable relative to the retracting member to shorten the axial extent of the retracting member to laterally retract a wound opening; and
a seal integral with the wound retractor, the seal including a chamber for receiving pressurized fluid to seal a retracted wound opening, and a sleeve having an inner sleeve section and an outer sleeve section with the chamber defined between the inner and outer sleeve sections, the outer sleeve section being substantially cylindrical, and the inner sleeve section being twisted and of the same untwisted diameter as that of the outer sleeve section.

18. A device as claimed in claim 17 wherein the proximal member comprises an annular ring assembly.

19. A device as claimed in claim 18 wherein the annular ring assembly comprises an inner ring and an outer ring between which the retracting member may be led.

20. A device as claimed in claim 19 wherein the inner ring defines a projection for location in a complementary recess of the outer ring with the retracting member located therebetween.

21. A device as claimed in claim 20 wherein the inner ring is a relatively loose fit in the recess of the outer ring.

22. A device as claimed in claim 20 wherein the inner ring is a relatively tight fit in the recess of the outer ring to grip the retracting member therebetween.

23. A device as claimed in claim 20 wherein at least a portion of one of the rings is movable from a rest position in which the retracting member is substantially clamped between the rings to a release position in which at least a portion of the retracting member is movable relative to the rings.

24. A device as claimed in claim 17 wherein the retracting member is provided by at least a portion of the outer sleeve section.

25. A device as claimed in claim 17 wherein the sleeve is turned axially back on itself to define the sleeve sections.

* * * * *